United States Patent [19]
Okaya

[11] Patent Number: 4,625,323
[45] Date of Patent: Nov. 25, 1986

[54] EQUIPMENT FOR SPECTRAL RADIOLOGY

[76] Inventor: Yoshiharu Okaya, 4 Wels La., East Setauket, N.Y. 11733

[21] Appl. No.: 533,113

[22] Filed: Sep. 19, 1983

[51] Int. Cl.⁴ .............................................. G03B 41/16
[52] U.S. Cl. ......................................... 378/82; 378/5; 378/145
[58] Field of Search ................. 378/82, 84, 85, 5, 145, 378/146

[56] References Cited

U.S. PATENT DOCUMENTS

| | | | |
|---|---|---|---|
| 2,543,630 | 2/1951 | Hansen | 378/84 |
| 2,853,617 | 9/1958 | Berreman | 378/84 |
| 3,229,089 | 1/1966 | Sasao | 378/85 |
| 3,517,194 | 6/1970 | Borkowski | 250/385 |
| 4,464,777 | 8/1984 | Machida | 378/146 |

OTHER PUBLICATIONS

Brown & Doniach, The Principles of X-Ray Absorption Spectroscopy, pp. 353-361.
Stern, Theory of the Extended X-Ray Absorption Fine Structure, 10/15/74, pp. 10, 3028-3037.
Lee & Pendry, Theory of the Extended X-Ray Absorption Fine Structure, 4/15/75, pp. 2795-2811.
Phizackerly & Matsushita, Development of an Energy Dispersive EXAFS Spectrometer for the Rapid Measurement of EXAFS Spectra, 1981, p. 12.
Elder, Hess, Tepperman & Shaw, EXAFS of Gold-Based Drugs Used to Treat Rheumatoid Arthritis, p. VII-118.

Primary Examiner—Craig E. Church
Assistant Examiner—Charles Wieland
Attorney, Agent, or Firm—Thomas L. Adams

[57] ABSTRACT

A machine for radiologically examining a patient employs a radiation source and a monochromator. The monochromator can reflect radiation from the source toward the patient. This monochromator is angularly positioned to narrow the bandwidth of the reflected radiation around a predetermined center wavelength. A discharge detector is positioned alongside the patient opposite the monochromator for producing a discharge in an electric field in response to receipt of the reflected radiation. Also included is a counting apparatus for measuring the extent of discharge in the discharge detector.

28 Claims, 8 Drawing Figures

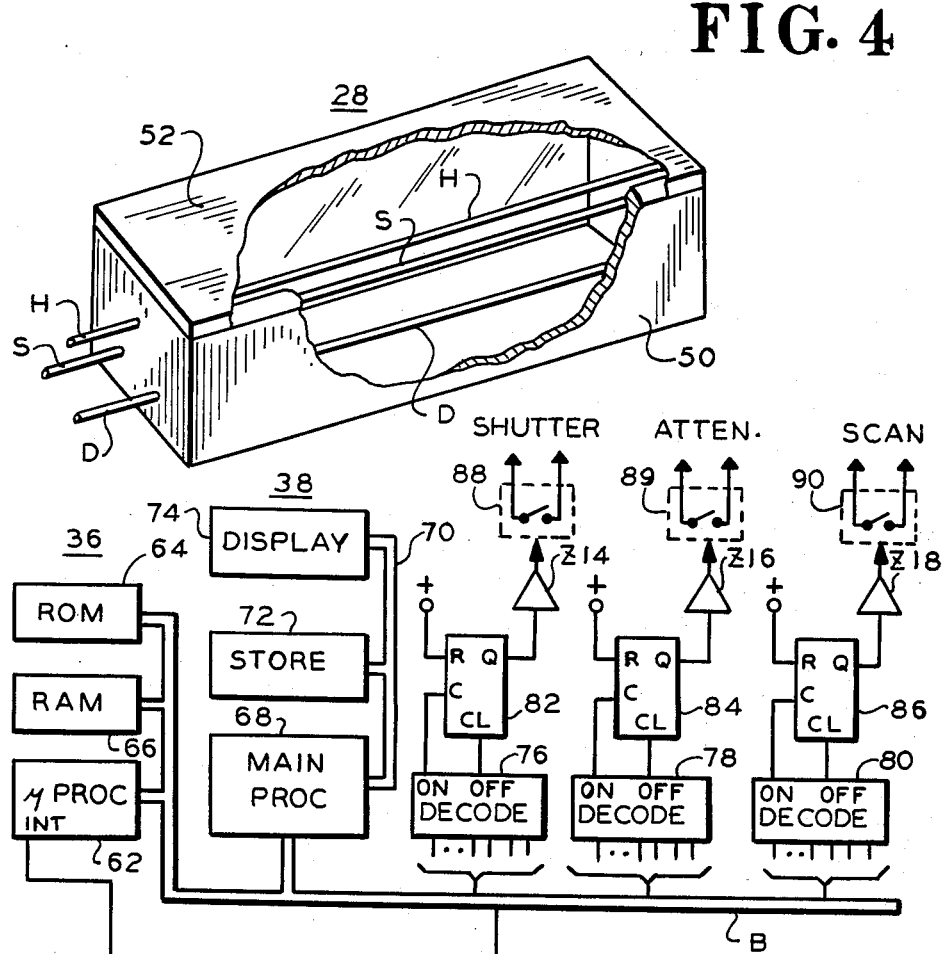
FIG. 4
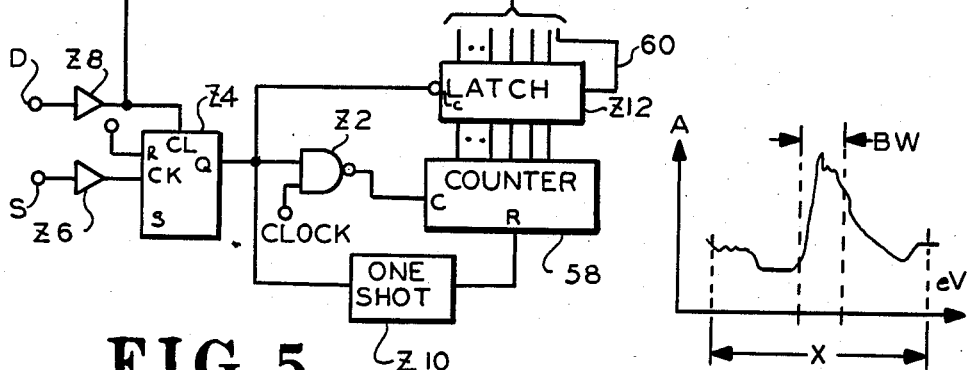
FIG. 5
FIG. 7

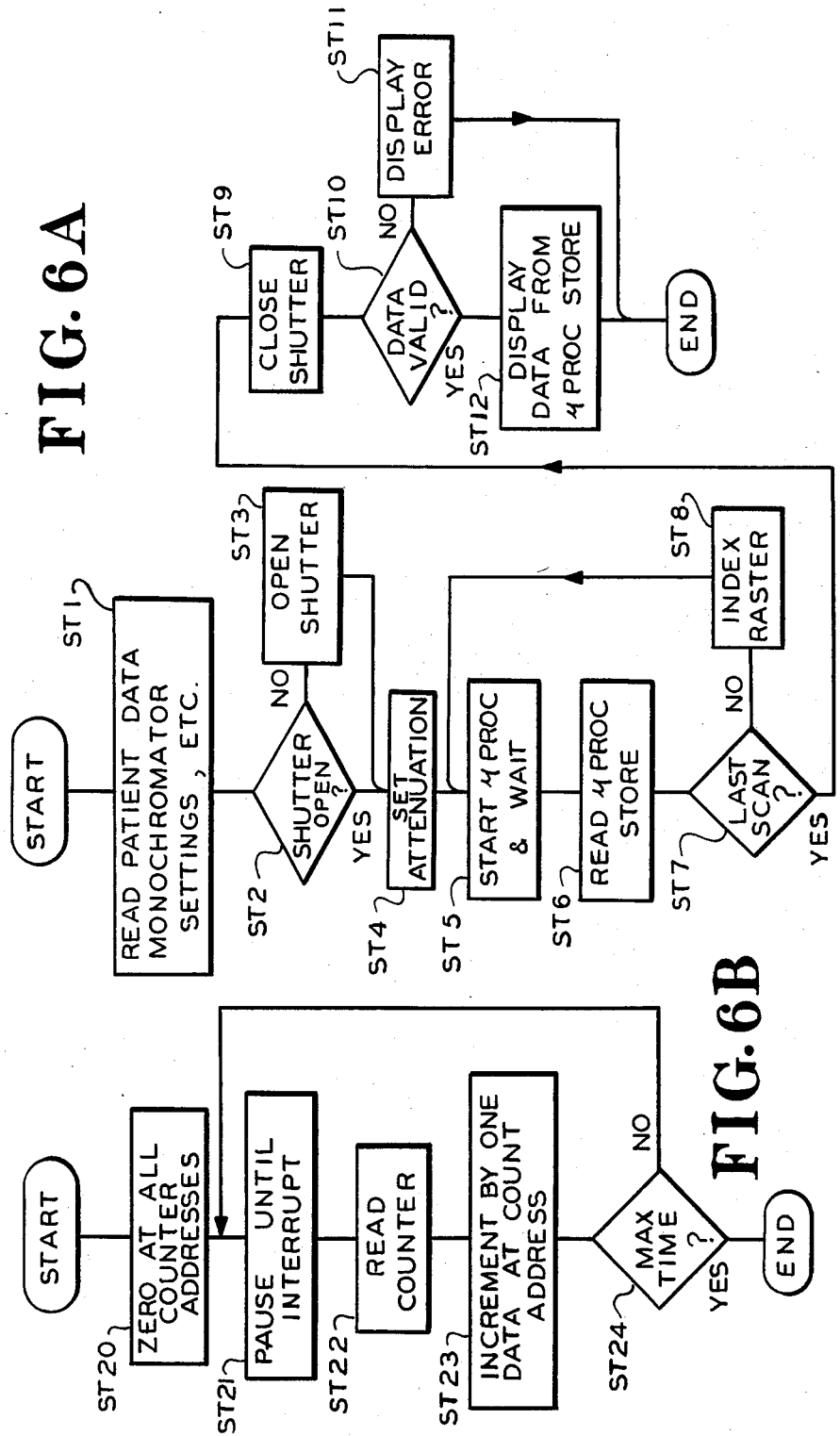

EQUIPMENT FOR SPECTRAL RADIOLOGY

BACKGROUND OF THE INVENTION

The present invention relates to equipment for radiologically examining a patient and, in particular, to radiological examination with a relatively narrow band of wavelengths.

Radiological examination of a patient can be performed with the familiar x-ray machine. A conventional x-ray photograph provides an image by detecting the different absorbing characteristics of tissues. However, this equipment operates over a relatively wide band of wavelengths so that its resolution and contrast are rather limited. Another disadvantage of conventional x-ray radiology is the need to work with photographic film. In addition to being expensive, such film requires dark room treatment and has a relatively slow, logarithmic response.

In a known radiological technique, a dye injected into a patient has a distinctive appearance on an x-ray photograph. The dye, when infused into the relevant tissue, adds contrast and reveals internal structure which would normally be lost under x-ray examination. However, these dyes often provide insufficient resolution to determine precise positions and concentrations. The specific absorption characteristic of a target or dye atom may exhibit a distinctive absorption feature only over a relatively narrow region (e.g., 100 to 200 eV) of its spectrum. Therefore, in order to study the behavior of this atom radiologically it would be advantageous to use only wavelengths in this energy region for optimum resolution and minimum exposure to the patient.

As an example of varying absorption spectra, the different valences of gold ($Au^+$ $Au^{+++}$ and $Au$) have distinctively different spectra, characteristic of the valence. It will be understood, therefore, that proper selection of a stain and the relevant energy range may indicate not only the presence or absence of the radiation absorbing stain, but also the mode of interaction between the atom and the tissue under examination.

A somewhat limited but so far the only method of determining molecular structure in a patient is radiating a sample with radio frequency waves to determine its nuclear magnetic resonance. Depending upon the spin characteristics of the target molecules, radio waves are absorbed and retransmitted in a characteristic pattern of wavelengths.

The literature also discusses absorption spectroscopy. For example, P. A. Lee and J. B. Pendry, Phys. Rev., Vol. B11, p. 2795 (1975); E. A. Stern, Phys. Rev., Vol. B10, p. 15 (1974); G. S. Brown and S. Doniach, The Principle of X-ray Absorption Spectroscopy, Synchrotron Research, Edited by H. Winick and S. Doniach, p. 353, Plenum Press (1980).

A known monochromator crystal can be positioned and bent to affect the wavelengths of reflected radiation. This principle operates in accordance with the well known Bragg's Law, which provides: $2d \sin \theta = n\lambda$ wherein $\theta$ is the angle of reflection with respect to normal, $\lambda$ is the wavelength, n is an integer and d the effective repetitive spacing of the crystal lattice. Regarding the bending of a crystal, see T. Matsushita and R. P. Phizackerly, Japanese J. Appl. Phys., Vol. 20, p. 2223 (1981).

SUMMARY OF THE INVENTION

In accordance with the illustrative embodiments demonstrating features and advantages of the present invention, there is provided a machine for radiologically examining a patient. This machine has a radiation source, a monochromator means and a detection means. The monochromator means can reflect radiation from the source toward the patient. This monochromator means is angularly positioned to narrow the bandwidth of its reflected radiation around a predetermined center wavelength. The detection means is positioned alongside the patient and opposite the monochromator means for detecting the reflected radiation.

Also in accordance with the same invention, a method is provided for radiologically examining a patient with a source of radiation and a reflective monochromator. The method includes the step of directing the source of radiation at the monochromator. The method also includes the step of angularly positioning the monochromator to reflect a narrowed bandwidth of the radiation at the patient. Another step of the method is measuring the extent of radiation passing through the patient.

By employing such equipment and methods an improved radiological examination of a patient can be performed. In a preferred embodiment, the monochromator is a germanium crystal that reflects a relataively narrow beam of x-rays toward a patient. Radiation transmitted through the patient is detected by an elongated conductor at a high voltage for producing a discharge effect. This discharge propels electrons onto a pair of parallel conductors. One of these conductors is an elongated delay line. Since the delay line is elongated, its delay, with respect to the other detecting line, corresponds to the linear position of the discharge.

In one embodiment the x-ray beam is collimated so that the spatial information determined by the discharge detector corresponds to different physical locations in the patient. In an alternate embodiment, the monochromator is bent to focus radiation at a point in the patient. Consequently, the spatial information determined by the detector corresponds to spectral information. In one embodiment, shutters and attenuators associated with the equipment are controlled by a main computer working together with a microprocessor. A preferred microprocessor employs a counter whose count corresponds to the delay between electrical output signals from the detector. Accordingly, the processor and counter can relieve a main processor from performing this repetitive task. The main computer, at the end of the scan, reads the stored data in the microprocessor and displays it in a tabular or graphical form, as desired.

BRIEF DESCRIPTION OF THE DRAWINGS

The above brief description, as well as other objects, features and advantages of the present invention, will be more fully appreciated by reference to the following detailed description of the presently preferred but nonetheless illustrative embodiments in accordance with the present invention when taken in conjunction with the accompanying drawings wherein:

FIG. 4 is a perspective view of the detector of FIG. 3 with portions thereof broken away for illustration purposes;

FIG. 5 is a schematic diagram of the processing and counting system associated with the apparatus of FIG. 1;

FIGS. 6A and 6B are flowcharts showing the operation of the main processor and microprocessor, respectively, of FIG. 1;

FIG. 7 is a spectral plot for a specific dye molecule.

DETAILED DESCRIPTION OF THE PREFERRED EMBODIMENT

Figure 1:
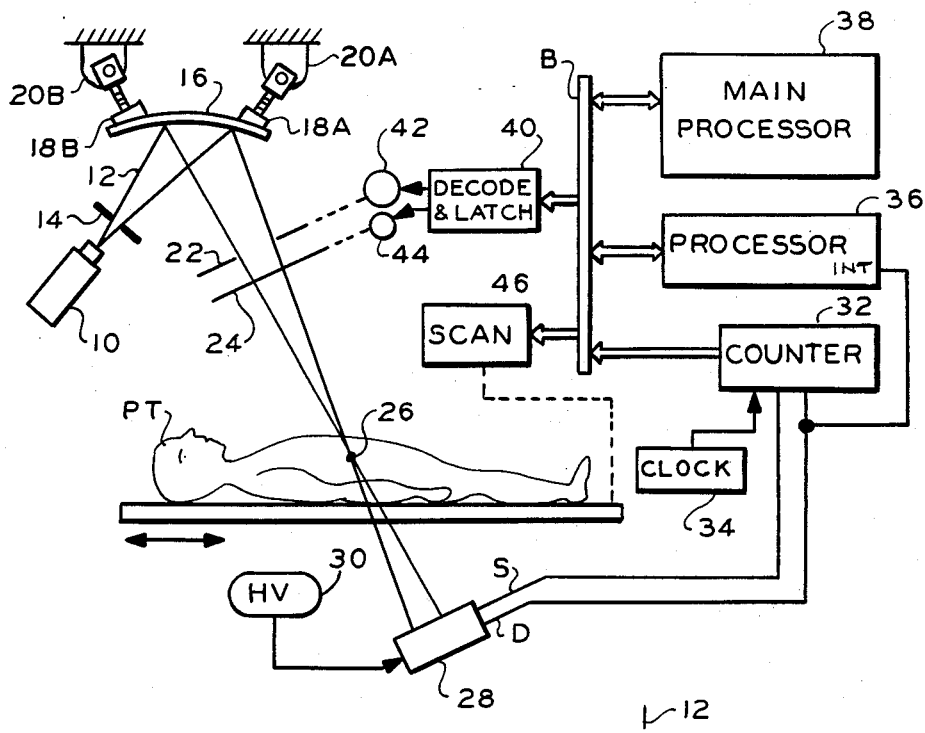
FIG. 1 is a schematic diagram of a radiological examining machine according to the principles of the present invention.

Referring to FIG. 1, a machine for radiologically examining patient PT employs radiation source 10. In this embodiment, source 10 provides a beam 12 of x-rays at an energy range exceeding 150 kV. Its cone of radiation is relatively narrow since source 10 has a diffraction-type of magnetic focus which restricts the beam to 40 degrees or less. A suitable source of x-rays can be obtained as a package from Shimadzu Medical & Scientific Instrument Corp. of Kyoto, Japan. Alternatively, where space and expense are not a limitation, a synchrotron can be used as device 10. Beam 12 is further restricted by aperture 14 placed before the output of source 10.

A monochromator means is shown herein as radiation reflecting crystal 16. In this embodiment, crystal 16 is a cylindrically bent, 99.5% pure germanium crystal having a (1, 1, 1) cut. The size of the crystal is greatly exaggerated merely for illustrative purposes, but in practical embodiments will be approximately 5 cm long, 1 cm wide and at least 0.3 cm thick.

Monochromator 16 is mounted at its two ends to bosses 18A and 18B, which are rotatably secured to overhead journals 20A and 20B, respectively. This illustrated structure is schematic, but demonstrates that bosses 18A and 18B can be rotated to establish the radius of curvature of crystal 16 and to cause reflective focusing of beam 12 at point 26 within patient PT. In one embodiment, the post-reflection angle of convergence is about, 0.05 radians, although clearly other angles can be chosen, depending upon the separation between crystal 16 and patient PT. The beam reflected off crystal 16 is transmitted through shutter 22 and an attenuator 24 before being focused. As described hereinafter in further detail, each point on monochromator 16 reflects radiation at essentially a single wavelength, which wavelength varies depending upon its circumferential position on monochromator 16. Accordingly, the reflected radiation has a spatially differing spectrum analagous to the spectral separation caused by a prism operating in the visible spectrum.

Approximately 40 cm past focal point 26 in patient PT, in one embodiment, is a discharge means 28 (also referred to as a detection means). Discharge means 28, as described further hereinafter, employs a high voltage source 30 (approximately 500 v) to produce a direct electrical signal on direct line S and a delayed electrical signal on delay line D. Lines S and D connect to a counting means, shown including counter 32, which receives an input from electronic clock generator 34. Counter 32 also has a plurality of data lines connected to bus B. Delay line D also connects directly to interrupt line INT of microprocessor 36, whose data lines also connect to bus B. A main processor 38, which may be a general purpose computer, a minicomputer, a sufficiently powerful microcomputer or a home computer, is shown with its data lines also connected to bus B. Also connected to bus B are the data lines of decoder and latch 40. A pair of outputs from decoder and latch 40 connect to electromechanical solenoids 42 and 44, which operate shutter 22 and position attenuator 24, respectively.

A scan means 46 is shown with a plurality of input data lines connected to bus B. Upon receiving a properly encoded signal on bus B, scan device 46 can mechanically shift table 48 upon which patient PT rests, by means of an internal stepper motor (not shown herein). The speed and distance incremented can be varied depending upon the amount of patient area which is to be scanned.

Figure 2:
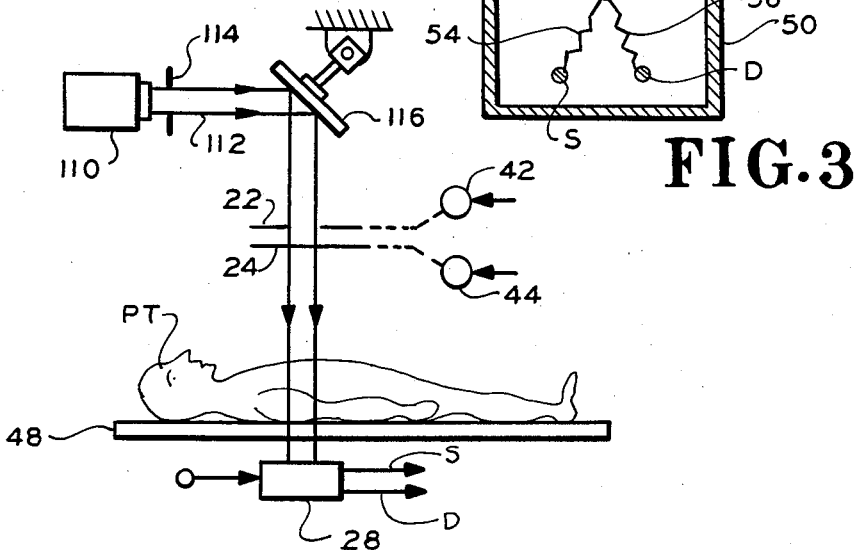
FIG. 2 is an schematic diagram of a machine which is an alternate to that of FIG. 1.

Referring to FIG. 2, an alternate embodiment shows an x-ray source 110. Source 110 can be similar to previously mentioned source 10, but includes magnetic focusing devices and appropriate collimating apertures to produce a collimated beam 112 of x-radiation which passes through aperture 114. Beam 112 is reflected from a flat monochromator 116, a crystal similar to crystal 16 of FIG. 1 except for the absence of bending. Beam 112 is reflected through aperture 22 and attenuator 24, which are identical to similarly numbered devices in FIG. 1. Again, devices 22 and 24 are controlled by solenoids 42 and 44, in a manner previously described. The reflected beam passing through patient PT and table 48 enters a discharge detector 28, which is similar to the detector previously mentioned.

As described hereinafter in further detail, the radiation reflected by flat monochromator 116 has a constant wavelength throughout the width of the beam. Since the beam does not focus within patient PT, the spatially distributed radiation received at detector 28 represents an image of the absorption patterns within patient PT.

Figure 3:
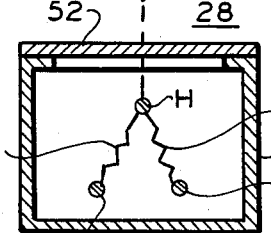
FIG. 3 is a transverse cross-sectional view of the detector of FIGS. 1 and 2.

Referring to FIGS. 3 and 4, the previously mentioned discharge means 28 is shown comprising an elongated, rectangular box 50, made of steel and held at ground potential. This one inch long box has a top open to provide an effective window length of about ⅞ inch. The height and width of box 50 are approximately ¼ inch each. Covering the top surface of box 50 is a mylar window 52 which is transparent to incident radiation beam 12. Window 52 is sealed to box 50 to form a gas-tight seal. The interior of box 50 is filled with an inert gas, such as krypton, which may contain a trace amount of carbon dioxide.

Embedded in and spanning across the two end walls of box 50 are a trio of insulated lines H, S and D. Wire H, referred to herein as a high voltage line, and wire S, referred to herein as a direct line, are copper wires about 20 mils in diameter. The wire D, referred to as a delay line, is capable of producing a maximum of 640 ns delay for electrons striking its distal end, due to its distributed conductive and capacitive components. Such delay line material can be purchased from Rigaku Denki, Inc. of Japan. High voltage line H is kept nominally at 500 volts while conductor S and D are kept nominally at ground or zero volts. Wires S and D are referred to herein as a spatial means.

Referring to FIG. 5, the previously mentioned counting means is shown herein as 16 bit counter 58 having its clock input C connected through NAND gate Z2 to a 50 or higher mHz clock signal at terminal CLOCK. The other input of NAND gate Z2 is connected to the Q output of R-S type flip-flop Z4, whose R input is connected to positive potential. Its clock input terminal CK and its reset input terminal CL are connected through buffer amplifiers Z6 and Z8, respectively, to previously identified lines S and D, respectively. The Q output of flip-flop Z4 is also connected through one shot Z10 to reset input R of counter 58. The data output lines of counter 58 are connected to the data setting inputs of latch Z12. This data can be clocked into latch Z12 by an input on its terminal C, which is connected to output Q of flip-flop Z4. Latch Z12 is able to transmit its stored data in response to an enabling signal applied to line 60. This line, together with the data output lines of latch Z12 are connected in parallel to previously mentioned data bus B.

A processing means is shown herein as a limited processor 62 in the form of an Intel sixteen bit microprocessor. Processor 62 has data inputs connected in parallel to bus lines B and an interrupt line connected to the output of buffer amplifier Z8. Connected to microprocessor 62 through bus lines B are memory components 64 and 66 in the form of read only (ROM) and random access (RAM) memories, respectively. Memories 64 and 66 contain the programming and the working storage, respectively, for microprocessor 62. Together, components 62, 64 and 66 (previously described as processor 36) comprise what is commonly referred to as a microcomputer and is of a conventional structure found in many existing systems, including home computer systems such as a TRS-80 computer by Radio Shack. The size of the memory is chosen to accomodate the programming instructions hereinafter described. Furthermore, sufficient working memory storage is provided to allow accumulation of the data hereinafter described, to a resolution required by the user. It is contemplated that for some embodiments memories 64 and 66 will each be 64 kilobytes.

Previously mentioned main processing means 38 is shown herein employing a main central processing unit 68 connected through a bus line 70 to a memory 72 and a display 74. The main processor 68 and storage 72 can be any general purpose computer, minicomputer, or sufficiently powerful microcomputer (for example, a H316 Honeywell general purpose computer or a home computer such as the TRS-80 by Radio Shack). Display 74 is a conventional terminal employing a cathode ray tube (CRT) and keyboard. The elements 66, 72 and 64 will have capacity sufficient to store and execute the programming steps hereinafter described. Main central processor 68 has an input/output port connecting to bus lines B so processor 68 can read or write data onto the bus lines or can be disconnected from it, depending upon programming instructions, to be described presently.

Connected in parallel across bus lines B are decoders 76, 78 and 80, each being a combinational logic circuit which responds to two unique codes, so that six codes altogether are detectable by the decoders. Detection of a relevant code is indicated by these decoders by a signal on its output terminals ON or OFF. Each of the ON lines of decoders 76, 78 and 80 are connected to the clock input C of R-S type flip-flops 82, 84 and 86, respectively. Each of the reset terminals CL of flip-flops 82, 84 and 86 connect to the OFF terminals of decoders 76, 78 and 80, respectively. The input terminal of buffer amplifiers Z14, Z16 and Z18 are connected to the Q outputs of flip-flops 82, 84 and 86, respectively, whose R inputs are each connected to positive potential. The outputs of buffer amplifiers Z14, Z16 and Z18 are connected to relay type circuits 88, 89 and 90, which each operate to close the illustrated contacts when positive potential is produced by the corresponding buffer amplifier. The closing of the contacts of relay 88 cause the shutter solenoid 42 to open the shutter 22 (FIGS. 1 and 5). The closure of the contacts of relay 89 cause attenuator solenoid 44 to remove the attenuator filter 24 (FIGS. 1 and 5). Closure of the contacts of relay 90 cause an incremental advancement of the electromechanical scanner 46 of FIG. 1. Additional decoders, flip-flops, buffer amplifiers and solenoids (not shown) may be used for other functions such as changes of scan directions and speeds.

To facilitate an understanding of the principles associated with the foregoing apparatus, its operation will now be briefly described (except for the apparatus of FIG. 2, which is described separately). Initially, patient PT is placed on table 48 which is positioned to one extreme so that subsequent mechanical scanning can occur. Before the program of main processor 38 is initiated, solenoids 42 and 44 keep shutter 22 closed and attenuator 24 in the position illustrated in FIG. 1. The radius of curvature of crystal monochromator 16 is set to reflect x-rays with a bandwidth of several hundred electron volts. The center wavelength is chosen to accomodate the probe or target molecule spectrum in patient PT, using Bragg's Law.

When the program of main processor 38 is initiated, it first enters subroutine ST1 (FIG. 6A) wherein data about the patient such as his name, the exposure time, the attenuator settings, the table scanning distance, the chosen monochromator setting, x-ray source settings and other pertinent data are provided by an operator as input through display terminal 74 (FIG. 5). This data can be used later in the program and can be provided as a heading for a subsequent data print-out. The program next executes step ST2 wherein the program determines whether the last command to the shutter was to open or close the shutter 22 (FIG. 1). If the shutter is not open, the program proceeds to step ST3, causing the shutter to open. Consequently, main processor 68 (FIG. 5) transmits a coded signal as output data to bus B. In response, decoder 76 senses the presence of a meaningful code and produces a signal on its ON line. In response, flip-flop 82 is clocked to produce a high output on its Q terminal which is applied through buffer amplifier Z14 to relay circuit 88 to open shutter 22. The next programming step ST4 (FIG. 6A) sets the attenuator 24 (FIG. 1). If the data entered in step ST1 required changing of the attenuator, an appropriate output signal is applied by main processor 68 (FIG. 5) to decoder 78. In response, decoder 78 could either produce a signal to cause output terminal Q of flip-flip 64 to go either high or low to remove or return attenuator 24, respectively, through the action of relay 89 and solenoid 44 (FIG. 1). Thereafter step ST5 is executed, which is a command for microprocessor 62 (FIG. 5) to start. By decoding an appropriate control command from processor 68 on bus line B, microprocessor 62 initiates its own internal program, contained in memory 64.

Referring to FIG. 6B, the microprocessor program is illustrated. Commencing with step ST20, microprocessor 62 inserts the number zero into each one of a predetermined number of addresses. These addresses correspond to the possible counts read from counter 58. Thereafter, step ST21 is executed which merely places the microprocessor into an idle condition until an interrupt signal is received. An interrupt is received as follows:

Once the shutter 22 has opened, radiation can be transmitted through patient PT to the discharge detector 28 (FIG. 1). As previously noted, the wavelengths are spatially distributed across the beam in a manner akin to the color separation produced by an optical prism. When the first photon of radiation strikes high voltage line H (FIGS. 3 and 4), an electron discharge occurs along paths 54 and 56 to induce electrons into lines S and D. Almost immediately, an electrical pulse is produced on line S. This electrical pulse is applied through buffer amplifier Z6 (FIG. 5) to clock flip-flop Z4 and produces a high output on its terminal Q. This high output initiates one shot Z10 to apply a relatively short pulse to input R of counter 58, thereby resetting it. Consequently, the continued high signal on line Q of flip-flop Z4 opens gate Z2 so that the pulses on terminal CLOCK can be counted by counter 58. The count on counter 58 therefore accumulates until the delayed pulse signal arrives at terminal D to drive buffer amplifier Z8. In response, reset input CL of flip-flop Z4 is triggered to produce a low output from terminal Q of flip-flop Z4. This falling signal stops the transmission of pulses from terminal CLOCK through NAND gate Z2. This falling signal also causes latch Z12 to store the accumulated count of counter 58.

It will be appreciated that this count is directly proportional to the delay interval between the signals on lines S and D (FIG. 4). Because the delay interval is related to the spatial separation between the output end of line D and the position on it where the discharge occurred, the delay information contains spectral information. As previously mentioned, the wavelengths entering detector 28 are distributed spatially similar to to the color separation caused by the well known optical prism.

The high signal occurring on the output of buffer amplifier Z8 (FIG. 5) also produces a high signal at interrupt terminal INT of microprocessor 62. This causes its program to index from step ST21 to ST22 (FIG. 6B) where the output of counter 58 is read. Consequently, microprocessor 62 provides a read signal on line 60 of bus B, allowing latch Z12 to transmit its data onto bus B for temporary storage in an appropriate accumulator register in microprocessor 62. Next, step ST23 (FIG. 6B) is executed wherein the data read from latch Z12 is treated as an address. The data existing at that address in memory 66 is fetched to the processor 62 which then increments the fetched data by one before returning it to the same address. Since the data at this address was initially set to zero (at step ST20 of FIG. 6B), the data at the address determined by latch Z12, for this first pass, is now set to one. Next, at step ST24 (FIG. 6B) the microprocessor 62 determines whether a maximum amount of time has expired. This may be performed by allowing the microprocessor at step ST21 to count the number of machine cycles expiring. Alternatively, an external clock can be read at step ST24 to determine whether the difference in time exceeds a preprogrammed maximum. If this maximum has not been exceeded (which will obviously be the case after one pass), the program will jump back to step ST21 to then repeat the cycle just described for microprocessor 62. In some embodiments the microprocessor program can be terminated early by the main processor 68 which may control an interrupt line of microprocessor 62.

The foregoing process will be a totaling of discharge events, each event being assigned to one spatial subinterval. For each discharge resulting in a particular count at counter 58, the number stored at the count address will be incremented by one. Thus, spatial integration will occur and will be stored in memory 66 (FIG. 5). Eventually the maximum time will have expired or the program interrupted so that the program of microprocessor 62 will end.

During the foregoing interval while the microprocessor program was being executed, the main processor was in the idled condition at step ST5. After an elapse of time sufficient to allow the microprocessor program to finish, the program of the main processor 68 will continue. This delay can be performed in a fashion similar to that described for the microprocessor or in response to a ready signal from it. Next, at step ST6 main processor 68 performs an input operation through bus line B and reads the contents of the random access memory 66 (FIG. 7) at those addresses corresponding to the possible counts from counter 58. Therefore, main processor 68 stores in its memory 72 all of the discharge events noted by microprocessor 62. Next, at step ST7 the main processor 68 determines whether patient table 48 (FIG. 1) ought to be incrementally moved. Since this is the first occurrence of this step, the table will normally be moved so that step ST8 will be executed (otherwise step ST9 is). In response to step ST8, processor 68 will produce an output on bus line B to decoder 80 causing its ON line to go high so that flip-flop 86, working through buffer amplifier Z18, closes relay contacts 90. As a result, the stepper motor of scanner 46 is indexed, causing table 48 to move incrementally. Thereafter, processor 68 issues through bus line B a code causing terminal OFF of decoder 80 to go high, thereby resetting flip-flop 86 to reopen the contacts of relay 90, to render table 48 (FIG. 1) quiescent.

Thereafter, step ST5 is reexecuted by the main processor 68. This step again causes microprocessor 62 to execute its program as shown in FIG. 6B. Accordingly, the main processor is again able to read another set of data corresponding to spectral data obtained at a different physical position in the patient. The loop comprising steps ST5-ST8 repeats a number of times determined by the data inputted at step ST1. When the number of incremental scans has reached the desired number, the program transfers from step ST7 to step ST9. Step ST9 calls for a closing of the shutter so that main processor 68 (FIG. 5) issues a coded signal through bus lines B which is decoded by decoder 76 to cause its OFF line to go high, thereby resetting flip-flop 82. In response, the contacts of relay 88 open so that shutter 22 (FIG. 1) is closed as solenoid 42 releases.

At step ST10, processor 68 checks each of the sets of data contained in its memory 72 to determine if each datum is within preprogrammed limits. The program also determines whether any of the data differs from its neighbor by some predetermined amount indicating a spurious response, which is then ignored and removed from the data set. If a majority of the data does not qualify, the program moves to step ST11 to display at terminal 74 (FIG. 5) an error message and end the main processor program. If valid, however, each of the data obtained from the microprocessor is appropriately scaled and presented in a tabular form in step ST12. These data will indicate the spectral absorption characteristics along a line in the patient. Alternatively, the data can be displayed graphically using well known output programming techniques. Once this data is transmitted to display terminal 74, the program of the main processor 68 ends.

As an example of the results and referring to FIG. 7, the spectral response to varying wavelengths of radiation is illustrated by a plot wherein the abscissa indicates in electron volts the wavelength of the incoming radiation. The absorption A by the patient is indicated along the ordinate. As shown in FIG. 7, the salient spectral response is concentrated in a relatively narrow bandwidth BW on the order of several hundred electron volts. In contrast, the bandwidth normally used by conventional x-ray machines is about 5,000 electron volts or the bandwidth indicated as interval X. The data obtained by the present apparatus lies within the bandwidth BW. Accordingly, the processor can provide a family of curves which will be similar in form to the curve illustrated for interval BW. Because only the distinctive data in bandwidth BW is examined, high resolution and contrast is obtained with small amount of radiation exposure.

Alternatively, the apparatus of FIG. 2 can be utilized. In this case, the programming is identical except that the tabulated data which is displayed at step ST12 may be considered a two-dimensional plot of the absorption coefficient over the patient. The reflection angle of monochromator 116 (FIG. 2) may be chosen to place its center wavelength near the peak of the characteristic illustrated in FIG. 7. In the latter case, scanning along the bandwidth BW is made by rotating monochromator 116 around a pivotal point (not shown in FIG. 2) and the bandwidth is determined by the rotating angle.

With either embodiment, a gold dye may be used, whose absorption edge can be determined, for example, with the apparatus of FIG. 1. It will be appreciated that the absorption edge for the various valences of gold (Au, Au$^+$, Au$^{++}$) is at about the same wavelength. These gold probe molecules may be useful in various radiological studies, for example, in kidney tissue studies.

It is significant to note that since the bandwidth can be greatly reduced, the total radiation to which the patient is exposed is drastically reduced. This, of course, is a great step forward in both sensitivity and safety.

It is to be appreciated that various modifications may be implemented with respect to the above-described preferred embodiments. For example, the apparatus comprising the microprocessor and counter could be replaced with a conventional multichannel data accumulator, for example, a 16 bit per channel device produced by Hewlett-Packard. Also, it will be appreciated that the above microprocessor and main processor can be replaced with various other computing machines. Indeed, in some simplified embodiments only one computer will be used instead of two. Also, the number of data bits used will depend upon the resolution required. Furthermore, the method of inputting and outputting data between the various peripherals and between the processors can be altered, depending upon the hardware used. Moreover, the programming steps can be supplemented or reduced to change the manner of operation. Also, the order in which certain steps are performed can be changed. The dimensions of the monochromator can be altered depending upon the area over which analysis is to be performed. Similarly, the curvature can be altered, depending upon the equipment spacing, the angles of convergence, etc. Also, various components illustrated herein can be replaced with alternate components to satisfy the desired speed, reliability, temperature stability, power handling capacity, etc.

Obviously, many modifications and variations of the present invention are possible in light of the above teachings. It is, therefore, to be understood that within the scope of the appended claims, the invention may be practiced otherwise than as specifically described.

What is claimed is:

1. A medical diagnostic machine for radiologically examining a living patient for a predetermined spectral feature indicative of predetermined absorption edges of target atoms in said living patient, comprising:

a radiation source for producing x-rays at an energy range suitable for medical diagnostic and having a spectrum suitable for producing images of the inside of said patient;

a monochromator means having a bent, radiation reflective crystal for reflectively focusing radiation from said source toward a point in said living patient, said radiation reflective crystal of said monochromator means being angularly positioned to narrow the bandwidth of its reflected radiation around a predetermined center wavelength;

patient supporting means for supporting said living patient at a position to intercept said x-rays reflected from said monochromator means; and a detection means position alongside said patient opposite said monochromator means for detecting said reflected radiation, said monochromator means being optically between said radiation source and said patient supporting means to irradiate the latter with reflections from said monochromator means, said bent, radiation reflective crystal being being to spatially distribute the spectrum of said reflected radiation across said detection means and to provide reflected radiation with a wavelength continuously, spatially and angularly variable over a bandwidth embracing said predetermined spectral feature.

2. A machine according to claim 1 wherein said detection means comprises:

a discharge means for producing a discharge in an electric field in response to receipt of said reflected radiation; and counting means for measuring the extent of discharge in said discharge means.

3. A machine according to claim 1 wherein said detection means includes:

spatial means for detecting the spatial separation between incoming quanta of radiation.

4. A machine according to claim 3 wherein said patient supporting means is operable to move said patient transversely to said reflected radiation, said detection means being operable as said patient supporting means is so moved to measure the spatial intensity of incident radiation at said detection means to provide spatially dependent data.

5. A machine according to claim 3 wherein said source produces a collimated beam.

6. A machine according to claim 2 wherein said discharge means includes:

a high voltage line extending transversely to said reflected radiation for intercepting it; and a direct line and a separate delay line, each having a terminal end and each being downstream from said high voltage line for producing an electrical discharge signal in response to discharge from said high voltage line, the electrical discharge signal of said delay line being delayed in accordance with the remoteness of its terminal end from the discharge of said high voltage line.

7. A machine according to claim 6 wherein said counting means is operable to resolve the delay of the signal from said delay line into one of a plurality of subintervals, said counting means being operable to measure the extent of discharge separately for each of the subintervals.

8. A machine according to claim 7 wherein said counting means comprises:
a clock;
a counter coupled to said clock and said direct and delay lines for measuring by said clock the time elapsing between the electrical discharge signals of said direct and delay lines; and
processing means coupled to said counter for cumulatively assigning each of said electrical discharge signals of said delay line to one of said subintervals so that each subinterval has an assigned cumulative value representing the extent of discharge occurring on a corresponding portion of said high voltage line.

9. A machine according to claim 8 wherein said processing means comprises:
a limited processor coupled to said counter for cumulatively assigning each of said electrical discharge signals of said delay line to one of said subintervals; and
main processing means for repetitively starting said limited processor and for reading and displaying its accumulated data.

10. A medical diagnostic method for radiologically examining a living patient for a predetermined spectral feature indicative of predetermined absorption edges of target atoms in said living patient, with a reflective monochromator having a bent, radiation reflective crystal and with a source of radiation for producing x-rays at an energy range suitable for medical diagnostics and having a spectrum suitable for producing images of the inside of said patient, comprising the steps of:
directing said source of radiation at said monochromator;
supporting said living patient at a position to intercept x-rays reflected from said monochromator;
angularly positioning said monochromator to reflectively focus at a point in said living patient a narrowed bandwidth of said radiation with a wavelength continuously, spatially and angularly variable over a bandwidth embracing said predetermined spectral feature; and
measuring on that side of said patient opposite said monochromator the extent of radiation passing through said patient at a position where the specturm of said radiation is spatially distributed.

11. A method according to claim 10 further comprising the step of:
measuring the spatial distribution of the radiation that has passed through said patient.

12. A method according to claim 11 further comprising the step of:
collimating the radiation from said source.

13. A method according to claim 12 further comprising the step of:
relatively moving said patient with respect to the reflected radiation to obtain spatially dependent data.

14. A method according to claim 11 further comprising the step of:
bending said monochromator to focus its reflected radiation on said patient and to separate spectrally the components of said reflected radiation so that measurement of said spatial distribution provides spectral data.

15. A method according to claim 11 employing a high voltage, direct and delay line and further comprising the steps of:
inserting said high voltage line in the path of said reflected radiation downstream of said patient to cause discharge;
sensing said discharge with said direct and delay line; and
resolving the spatial distribution of said discharge by the delay between signals on said direct and delay line.

16. A medical diagnostic machine for radiologically examining a living patient for a predetermined spectral feature indicative of predetermined absorption edges of target atoms in said living patient, comprising:
a radiation source for producing x-rays at an energy range suitable for medical diagnostics and having a spectrum suitable for producing images of the inside of said patient;
a monochromator means having a flat, radiation reflective crystal for reflecting radiation from said source toward said living patient, said radiation reflective crystal of said monochromator means being rotatably mounted and angularly positioned to narrow the bandwidth of its reflected radiation around a predetermined center wavelength;
patient supporting means for supporting said living patient at a position to intercept said x-rays reflected from said monochromator means; and
a detection means positioned alongside said patient opposite said monochromator means for detecting said reflected radiation, said monochromator means being optically between said radiation source and said patient supporting means to irradiate the latter with reflections from said monochromator means; said flat, radiation reflective crystal being rotatable to select and to spatially disturbute a discrete wavelength of said reflected radiation across said patient supporting means and said detection means, said discrete wavelength being adjustable over a bandwidth embracing said predetermined spectral feature.

17. A machine according to claim 16 wherein said detection means comprises:
a discharge means for producing a discharge in an electric field in response to receipt of said reflected radiation; and
counting means for measuring the extent of discharge in said discharge means.

18. A machine according to claim 17 wherein said discharge means includes:
a high voltage line extending transversely to said reflected radiation for intercepting it; and
a direct line and a separate delay line, each having a terminal end and each being downstream from said high voltage line for producing an electrical discharge signal in response to discharge from said high voltage line, the electrical discharge signal of said delay line being delayed in accordance with the remoteness of its terminal end from the discharge of said high voltage line.

19. A machine according to claim 18 wherein said counting means is operable to resolve the delay of the signal from said delay line into one of a plurality of subintervals, said counting means being operable to measure the extend of discharge separately for each of the subintervals.

20. A machine according to claim 19 wherein said counting means comprises:
a clock;
a counter coupled to said clock and said direct and delay lines for measuring by said clock the time elapsing between the electrical discharge signals of said direct and delay lines; and
processing means coupled to said counted for cumlatively assigning each of said electrical discharge signals of said delay line to one of said subintervals so that each subinterval has an assigned cumulative value representing the extent of discharge occurring on a corresponding portion of said high voltage line.

21. A machine according to claim 20 wherein said processing means comprises:
a limited processor coupled to said counter for cumulatively assigning each said electrical discharge signals of said delay line to one of said subintervals; and
main processing means for repetitively starting said limited processor and for reading and displaying its accumulated data.

22. A machine according to claim 16 wherein said detection means includes:
spatial means for detecting the spatial separation between incoming quanta of radiation.

23. A machine according to claim 22 wherein said patient supporting means is operable to move said patient transversely to said reflected radiation, said detection means being operable as said patient supporting means is so moved to measure the spatial intensity of incident radiation at said detection means to provide spatially dependent data.

24. A medical diagnostic method for radiologically examining a living patient for a predetermined spectral feature indicative of predetermined absorption edges of target atom in said living patient, with a reflective monochromator having a flat, radiation reflective crystal and with a source of x-rays having a spectrum suitable for producing images of the inside of said patient, comprising the steps of:
directing said source of x-rays at said monochromator;
supporting said living patient at a position to intercept x-rays reflected from said monochromator;
angularly adjusting said monochromator to reflect across said living patient a narrowed bandwidth of said x-rays containing a discrete wavelength that is continuously adjustable over a bandwidth embracing said predetermined spectral feature; and
measuring on that side of said patient opposite said monochromator the extend of x-rays passing through said patient, at a position where said discrete wavelength of said radiation is spatially distributed.

25. A method according to claim 24 further comprising the step of:
measuring the spatial distrubution of the radiation that has passed through said patient.

26. A method according to claim 25 further comprising the step of:
relatively moving said patient with respect to the reflected radiation to obtain spatially dependent data.

27. A method according to claim 25 further comprising the step of:
rotating said monochromator to obtain spectral data as a function of rotational angle.

28. A method according to claim 25 employing a high voltage, direct and delay line and further comprising the steps of:
inserting said high voltage line in the path of said reflected radiation downstram of said patient to cause discharge;
sensing said discharge with said direct and delay line; and
resolving the spatial distribution of said discharge by the delay between signals on said direct and delay line.

* * * * *